United States Patent
Yamada

(10) Patent No.: US 7,301,011 B2
(45) Date of Patent: Nov. 27, 2007

(54) AZO COMPOUND AND TAUTOMER THEREOF

(75) Inventor: Satoru Yamada, Shizuoka-ken (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/476,611

(22) Filed: Jun. 29, 2006

(65) Prior Publication Data

US 2007/0015912 A1 Jan. 18, 2007

(30) Foreign Application Priority Data

Jun. 30, 2005 (JP) ............................ 2005-192159

(51) Int. Cl.
*C09B 44/16* (2006.01)
(52) U.S. Cl. .................................................. 534/610
(58) Field of Classification Search ................. 534/610
See application file for complete search history.

(56) References Cited

U.S. PATENT DOCUMENTS

| 3,899,478 A | * | 8/1975 | Fleckenstein et al. | ....... 534/607 |
| 4,066,637 A | * | 1/1978 | Ramanthan | .................. 534/604 |
| 7,108,743 B2 | * | 9/2006 | Fujiwara et al. | ......... 106/31.48 |

FOREIGN PATENT DOCUMENTS

| DE | 198 05 544 A1 | 8/1999 |
| JP | 4-59287 A | 2/1992 |
| JP | 4-201483 A | 7/1992 |
| JP | 2002-129047 A | 5/2002 |
| JP | 2004-99802 | * | 4/2004 |

OTHER PUBLICATIONS

J. Fabian and H. Hartmann, "Light Absorption of Organic Colorants", VII. Azo Dyes, Springer-Verlag, Berlin, 1980.

\* cited by examiner

*Primary Examiner*—Fiona T Powers
(74) *Attorney, Agent, or Firm*—Sughrue Mion Pllc.

(57) ABSTRACT

An azo compound and tautomer thereof represented by the following formula (1) or the formula (2):

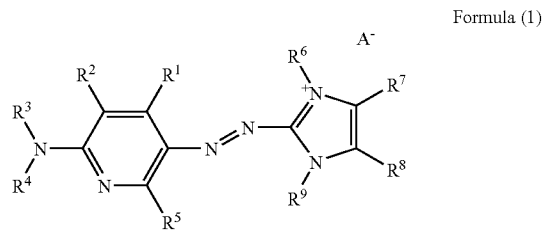

Formula (1)

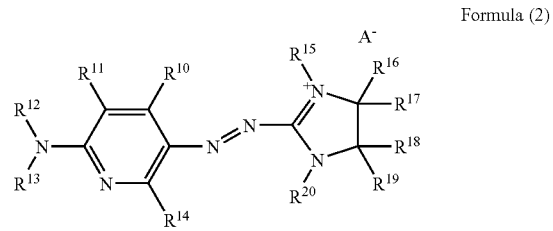

Formula (2)

wherein $R^1$, $R^2$, $R^5$, $R^7$, $R^8$, $R^{10}$, $R^{11}$, $R^{14}$, $R^{16}$, $R^{17}$, $R^{18}$, and $R^{19}$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom; $R^3$, $R^4$, $R^6$, $R^9$, $R^{12}$, $R^{13}$, $R^{15}$, and $R^{20}$ each independently represents a hydrogen atom, alkyl group, or aryl group; $R^1$ and $R^2$, $R^2$ and $R^3$, $R^3$ and $R^4$, $R^6$ and $R^7$, $R^7$ and $R^8$, $R^8$ and $R^9$, $R^{10}$ and $R^{11}$, $R^{11}$ and $R^{12}$, $R^{12}$ and $R^{13}$, $R^{15}$ and $R^{16}$, $R^{16}$ and $R^{17}$, $R^{17}$ and $R^{18}$, $R^{18}$ and $R^{19}$, and $R^{19}$ and $R^{20}$ may join to each other to form a ring structure, and $A^-$ represents a counter anion.

9 Claims, No Drawings

AZO COMPOUND AND TAUTOMER THEREOF

CROSS-REFERENCE TO RELATED APPLICATION

This application claims priority under 35USC 119 from Japanese Patent Application No. 2005-192159, the disclosure of which is incorporated by reference herein.

BACKGROUND OF THE INVENTION

1. Field of the Invention

The present invention concerns a novel azo compound and, in particular, it relates to a novel azo dye and a tautomeric isomer thereof having favorable hue and light fastness.

2. Description of the Related Art

Since azo compounds have absorption of various visible lights, they have conventionally been used in various fields as dyes. Azo compounds have been used, for example, for coloration of synthetic resins, printing inks, sublime thermal transfer material dyes and ink jet recording inks and have also been used recently in the field of electronics as functional dyes.

One of the important properties required of azo compounds as dyes is the absorption spectrum. The hue of a dye gives an effect on the color and aesthetic property of an article to be colored by the dye and has a significant visual effect. Accordingly, studies on the absorption spectra of dyes have long been widely studied and are described in literature such as "Light Absorption of Organic Colorants" by J. Fabian and H. Hartmann (Springer-Verlag, Berlin, 1980).

Further, performances required of dyes have become varied depending on the application use. It has been required for dyes to have a plurality of functions depending on the application uses in many cases, such that, for example, a dye of brilliant hue and favorable dyeability is desired when dying sheep skins or cow skins, and a dye of less water solubility and of brilliant hue is desired to allow laundry in the case of clothing ornaments. In addition, in the case of use, particularly, for printing inks, sublime thermal transfer material dyes and ink jet recording inks, it has been strongly demanded that durability against light (light fastness) under various environmental conditions is high, in addition to brilliant hue.

In order to solve the improvement of the light fastness of a dye, various diazo compounds or couplers are disclosed (for example in Japanese Patent Application Laid open (JP-A) No. 4-59287 and JP-A No. 4-201483. While the light fastness is improved to some extent thereby, it is not yet sufficient and there remains room for further improvement of light fastness.

Further, as an attempt to improve the light fastness, azo dyes containing quaternary salts have been proposed (for example, in JP-A No. 2002-129047 and the specification of DE No. 19805554). However, these still provide only slight improvements and satisfactory light fastness performance has not yet been attained.

As described above, it is important for dyes to be capable of maintaining brilliance and density even when they are exposed to light or the like for a long time, and at present no azo dye compounds having favorable light resistant performance have yet been provided by the existing techniques described above.

SUMMARY OF THE INVENTION

The present invention has been made in view of the above circumstances and provides an azo compound and tautomer thereof represented by the following formula (1) or formula (2):

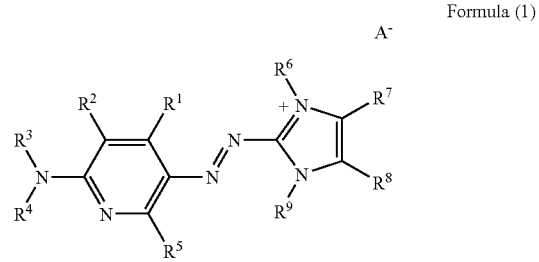

Formula (1)

wherein $R^1$, $R^2$, $R^5$, $R^7$, and $R^8$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom; $R^3$, $R^4$, $R^6$, and $R^9$ each independently represents a hydrogen atom, alkyl group, or aryl group; $R^1$ and $R^2$, $R^2$ and $R^3$, $R^3$ and $R^4$, $R^6$ and $R^7$, $R^7$ and $R^8$, and $R^8$ and $R^9$ may join to each other to form a ring structure; and $A^-$ represents a counter anion.

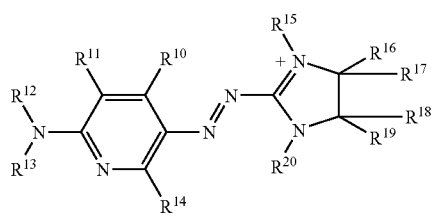

Formula (2)

wherein $R^{10}$, $R^{11}$, $R^{14}$, $R^{16}$, $R^{17}$, $R^{18}$, and $R^{19}$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group or halogen atom; $R^{12}$, $R^{13}$, $R^{15}$, and $R^{20}$ each independently represents a hydrogen atom, alkyl group, or aryl group; $R^{10}$ and $R^{11}$, $R^{11}$ and $R^{12}$, $R^{12}$ and $R^{13}$, $R^{15}$ and $R^{16}$, $R^{16}$ and $R^{17}$, $R^{17}$ and $R^{18}$, $R^{18}$ and $R^{19}$, and $R^{19}$ and $R^{20}$ may join to each other to form a ring structure; and $A^-$ represents a counter anion.

DETAILED DESCRIPTION OF THE INVENTION

An azo compound of the invention is to be described. The azo compound of the invention includes tautomer thereof.

The azo compound of the first invention is a compound represented by the following formula (1) and tautomer thereof (including azo dye), which is suitable as azo dyes of excellent light fastness.

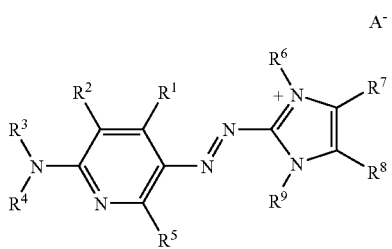

Formula (1)

In the formula (1), $R^1$, $R^2$, $R^5$, $R^7$, and $R^8$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom. $R^3$, $R^4$, $R^6$ and $R^9$ each independently represents a hydrogen atom, alkyl group, or aryl group. $R^1$ and $R^2$; $R^2$ and $R^3$; $R^3$ and $R^4$; $R^6$ and $R^7$; $R^7$ and $R^8$; and $R^8$ and $R^9$ may join to each other to form a ring structure, $A^-$ represents a counter anion.

The alkyl group represented by $R^1$, $R^2$, $R^3$, $R^4$, $R^5$, $R^6$, $R^7$, $R^8$, and $R^9$ may be not-substituted or have a substituent. In a case where the alkyl group further has a substituent, the substituent is, for example, preferably an alkyl group, phenyl group, halogen atom, alkoxy group, aryloxy group, alkoxy carbonyl group, acyloxy group, acylamino group, carbamoyl group, cyano group, carboxylic acid group, sulfonic acid group, or heterocyclic group, and more preferably, a methyl group or butyl group.

The alkyl group represented by $R^1$, $R^2$, $R^3$, $R^4$, $R^5$, $R^6$, $R^7$, $R^8$, and $R^9$ include preferably, for example, a methyl group, ethyl group, normal propyl group, isopropyl group, normal butyl group, isobutyl group, tertiary butyl group, pentyl group, cyclopentyl group, hexyl group, cyclohexyl group, heptyl group, octyl group, tertiary octyl group, 2-ethylhexyl group, decyl group, dodecyl group, octadecyl group.

As the alkyl group represented by $R^1$, $R^2$, $R^3$, $R^4$, $R^5$, $R^6$, $R^7$, $R^8$, and $R^9$, alkyl groups having 1 to 20 carbon atoms are preferred, alkyl groups having 1 to 15 carbon atoms are more preferred, alkyl groups having 1 to 10 carbon atoms are further preferred, and a methyl group or heptyl group is particularly preferred.

The aryl group represented by $R^1$, $R^2$, $R^3$, $R^4$, $R^5$, $R^6$, $R^7$, $R^8$, and $R^9$ may be not-substituted or have a substituent. As the aryl group, aryl groups having 6 to 25 carbon atoms are preferred, aryl groups having 6 to 10 carbon atoms are more preferred and, further, not-substituted or substituted phenyl groups are preferred. In a case where the aryl group has a substituent, the substituent is, for example, preferably an alkyl group, phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

As the aryl group represented by $R^1$, $R^2$, $R^3$, $R^4$, $R^5$, $R^6$, $R^7$, $R^8$, and $R^9$, phenyl group, 2,4,6-trimethoxyphenyl group, or 2,6-isopropylphenyl group is particularly preferred.

The alkoxy group represented by $R^1$, $R^2$, $R^5$, $R^7$, and $R^8$ may be not-substituted or have a substituent. In a case where the alkoxy group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The alkoxy group represented by $R^1$, $R^2$, $R^5$, $R^7$, and $R^8$ preferably includes, for example, a methoxy group, ethoxy group, normal propyloxy group, isopropyloxy group, normal butyloxy group, isobutyloxy group, tertiary butyloxy group, pentyloxy group, cyclopentyloxy group, hexyloxy group, cyclohexyloxy group, heptyloxy group, octyloxy group, tertiary octyloxy group, 2-ethylhexyloxy group, decyloxy group, dodecyloxy group, octadecyloxy group, 1-ethylpropyloxy group, or 2-methyl-4,4-dimethylpentyloxy group.

As the alkoxy group represented by $R^1$, $R^2$, $R^5$, $R^7$, and $R^8$, alkoxy groups having 1 to 20 carbon atoms are preferred, alkoxy groups having 1 to 15 carbon atoms are more preferred, and a methoxy group is particularly preferred.

The aryloxy group represented by $R^1$, $R^2$, $R^5$, $R^7$, and $R^8$, may be not-substituted or have a substituent. As the aryloxy group, aryloxy groups having 6 to 25 carbon atoms are preferred, aryloxy groups having 6 to 10 carbon atoms are more preferred and, further, not-substituted or substituted phenoxy groups are preferred. In a case where the aryloxy group further has a substituent, the substituent is, for example, preferably an alkyl group, phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

As the aryloxy group represented by $R^1$, $R^2$, $R^5$, $R^7$, and $R^8$, a phenoxy group is particularly preferred.

The alkylsulfonyl group represented by $R^1$, $R^2$, $R^5$, $R^7$, and $R^8$ may be not substituted or have a substituent. In a case where the alkylsulfonyl group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The alkylsulfonyl group represented by $R^1$, $R^2$, $R^5$, $R^7$, and $R^8$ preferably includes, for example, a methylsulfonyl group, ethylsulfonyl group, normal propylsulfonyl group, isopropylsulfonyl group, normal butylsulfonyl group, isobutylsulfonyl group, tertiary butylsulfonyl group, pentylsulfonyl group, cyclopentylsulfonyl group, hexylsulfonyl group, cyclohexylsulfonyl group, heptylsulfonyl group, octylsulfonyl group, tertiary octylsulfonyl group, 2-ethylhexyl sulfonyl group, decylsulfonyl group, dodecylsulfonyl group, or octadecylsulfonyl group.

As the alkylsulfonyl group represented by $R^1$, $R^2$, $R^5$, $R^7$, and $R^8$, alkylsulfonyl groups having 1 to 20 carbon atoms are preferred, alkylsulfonyl groups having 1 to 15 carbon atoms are more preferred, alkylsulfonyl groups having 1 to 10 carbon atoms are further preferred, and a methylsulfonyl group is particularly preferred.

The arylsulfonyl group represented by $R^1$, $R^2$, $R^5$, $R^7$, and $R^8$ may be not-substituted or have a substituent. As the arylsulfonyl group, arylsulfonyl groups having 6 to 25 carbon atoms are preferred, arylsulfonyl groups having 6 to 10 carbon atoms are more preferred and, further, not-substituted or substituted phenyl sulfonyl groups are preferred.

In a case where the arylsulfonyl group represented by $R^1$, $R^2$, $R^5$, $R^7$, and $R^8$ further has a substituent, the substituent is, for example, preferably, an alkyl group, phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

As the arylsuofonyl group represented by $R^1$, $R^2$, $R^5$, $R^7$, and $R^8$, 4-methylphenylsulfonyl group is particularly preferred.

The alkylthio group represented by $R^1$, $R^2$, $R^5$, $R^7$, and $R^8$ may be not-substituted or have a substituent. In a case where the alkylthio group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The alkylthio group represented by $R^1$, $R^2$, $R^5$, $R^7$, and $R^8$, preferably includes, for example, a methylthio group, ethylthio group, normal propylthio group, isopropylthio group, normal butylthio group, isobutylthio group, tertiary butylthio group, pentylthio group, cyclopentylthio group, hexylthio group, cyclohexylthio group, heptylthio group, octylthio group, tertiary octylthio group, 2-ethylhexylthio group, decylthio group, dodecylthio group, or octadecylthio group.

As the alkylthio group represented by $R^1$, $R^2$, $R^5$, $R^7$, and $R^8$, alkylthio groups having 1 to 20 carbon atoms are preferred, alkylthio groups having 1 to 15 carbon atoms are more preferred, alkylthio groups having 1 to 10 carbon atoms are further preferred, a methylthio group is particularly preferred.

The arylthio group represented by $R^1$, $R^2$, $R^5$, $R^7$, and $R^8$ may be not-substituted or have a substituent. As the arylthio group, arylthio groups having 6 to 25 carbon atoms are preferred, arylthio groups having 1 to 15 carbon atoms are more preferred and, further, not-substituted or substituted phenyl groups are preferred.

In a case where the arylthio group represented by $R^1$, $R^2$, $R^5$, $R^7$, and $R^8$ further has a substituent, the substituent is, for example, preferably an alkyl group, phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The arylthio group represented by $R^1$, $R^2$, $R^5$, $R^7$, and $R^8$, a phenylthio group is particularly preferred.

The acyl group represented by $R^1$, $R^2$, $R^5$, $R^7$, and $R^8$ may be not-substituted or have a substituent. In a case where the acyl group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The acyl group represented by $R^1$, $R^2$, $R^5$, $R^7$, and $R^8$, preferably includes, for example, methyl carbonyl group, ethyl carbonyl group, normal propyl carbonyl group, isopropyl carbonyl group, normal butyl carbonyl group, isobutyl carbonyl group, tertiary butyl carbonyl group, pentyl carbonyl group, cyclopentyl carbonyl group, hexyl carbonyl group, cyclohexyl carbonyl group, heptyl carbonyl group, octyl carbonyl group, tertiary octylthio group, 2-ethylhexyl carbonyl group, decyl carbonyl group, dodecyl carbonyl group, octadecyl carbonyl group, 1-ethylpropyl carbonyl group, or 2-methyl-4,4-dimethylpentyl carbonyl group.

As the acyl group represented by $R^1$, $R^2$, $R^5$, $R^7$, and $R^8$, acyl groups having 1 to 20 carbon atoms are preferred, acyl groups having 1 to 15 carbon atoms are more preferred and a methylcarbonyl group is particularly preferred.

The carbamoyl group represented by $R^1$, $R^2$, $R^5$, $R^7$, and $R^8$ may be not-substituted or have a substituent. In a case where the carbamoyl group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The carbamoyl group represented by $R^1$, $R^2$, $R^5$, $R^7$, and $R^8$, preferably includes, for example, methyl carbamoyl group, ethyl carbamoyl group, normal propyl carbamoyl group, isopropyl carbamoyl group, normal butyl carbamoyl group, isobutyl carbamoyl group, tertiary butyl carbamoyl group, pentyl carbamoyl group, cyclopentyl carbamoyl group, hexyl carbamoyl group, cyclohexyl carbamoyl group, heptyl carbamoyl group, octyl carbamoyl group, tertiary octyl carbamoyl group, 2-ethylhexyl carbamoyl group, dimethyl carbamoyl group, diethyl carbamoyl group, dinormal propyl carbamoyl group, diisopropyl carbamoyl group or dinormalbbutyl carbamoyl group.

As the carbamoyl group represented by $R^1$, $R^2$, $R^5$, $R^7$, and $R^8$, carbamoyl groups having 1 to 20 carbon atoms are preferred, carbamoyl groups having 1 to 15 carbon atoms are more preferred, and methyl carbamoyl group is particularly preferred.

The amino group represented by $R^1$, $R^2$, $R^5$, $R^7$, and $R^8$ may be no-substituted or have a substituent. In a case where the amino group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The amino group represented by $R^1$, $R^2$, $R^5$, $R^7$, and $R^8$ may be primary or secondary and preferably includes, for example, methylamino group, ethylamino group, normal propylamino group, isopropylamino group, normal butylamino group, isobutylamino group, tertiary butylamino group, pentylamino group, cyclopentylamino group, hexylamino group, cyclohexylamino group, heptylamino group, octylamino group, tertiary octylamino group, 2-ethylhexylamino group, dimethylamino group, diethylamino group, dinormal propylamino group, diisopropylamino group, dinormal butylamino group, phenylamino group, or tolylamino group.

As the amino group represented by $R^1$, $R^2$, $R^5$, $R^7$, and $R^8$, amino groups having 1 to 20 carbon atoms are preferred, amino groups having 1 to 15 carbon atoms are more preferred, and a phenylamino group is particularly preferred.

As the halogen atom represented by $R^1$, $R^2$, $R^5$, $R^7$, and $R^8$ includes preferably, for example, F, Cl, Br and I. Cl is particularly preferred.

In the formula (I), $R^1$ and $R^2$, $R^2$ and $R^3$, $R^3$ and $R^4$, $R^6$ and $R^7$, $R^7$ and $R^8$, and $R^8$ and $R^9$ may join to each other to form a ring structure. The ring structure includes, for example, pyrrolidine group, indoline group, cyclohexyl group, pyrazine group, and benzene.

In the formula (1), $A^-$ represents a counter anion. The counter anion represented by $A^-$ is not particularly restricted so long as it can form a counter anion, and it may be either a monoanion or polyvalent anion, and may be either an inorganic anion or organic anion. Specifically, $Cl^-$, $Br^-$, or $I^-$, sulfate anion of 1 to 20 carbon atoms, carbonate anion of 2 to 21 carbon atoms, alkyl sulfate ion, hexafluoro phosphate ion, tetrafluoro borate ion, perchlorate ion, carbonate ion, or sulfate ion is preferred, and hexafluoro phosphate ion is more preferred.

In a case where $R^6$ or $R^9$ has a substituent, the substituent may form a salt instead of the counter anion represented by $A^-$ in which the azo compound is constituted as an intramolecular salt. In a case where the substituent forms a salt instead of the counter anion represented by $A^-$, the azo compound of the invention may not have $A^-$.

A preferred embodiment of the azo compound of the first invention includes:
(1) an embodiment in which $R^6$ and $R^9$ represent aryl groups,
(2) an embodiment in which $R^3$ and $R^4$ represent an alkyl group or an aryl group,
(3) an embodiment in which $R^2$, $R^5$, $R^7$, and $R^8$ each independently represents a hydrogen atom, alkyl group, or aryl group, and
(4) an embodiment in which each of $R^2$, $R^5$, $R^7$ and $R^8$ represents hydrogen atom.

In the invention, each of the embodiments (1) to (4), or an embodiment having a combination of (1) to (2) and (3) or (4) is preferred.

Specifically, a preferred embodiment of the azo compound of the first invention is an embodiment in which $R^1$ represents an alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom and each of $R^2$ and $R^5$, $R^7$ and $R^8$ represents hydrogen atom; or an embodiment in which $R^1$ represents a methyl group and each of $R^2$, $R^5$, $R^7$, and $R^8$ represents hydrogen atom in $R^1$, $R^2$, $R^3$, $R^4$, $R^5$, $R^6$, $R^7$, $R^8$, and $R^9$. Further, for $R^3$ and $R^4$, an embodiment in which $R^3$ and $R^4$ represent butyl group, cyclobutyl group, dibutyl carbamoyl methyl group or butyloxycarbonylmethyl group, or represent a pyrrolidine ring, or indoline ring in a case of cyclic structure is particularly preferred.

The azo compound of the second invention is a compound represented by the following formula (2) and tautomer thereof (including azo dyes), which is suitable as azo dyes of excellent light fastness.

Formula (2)

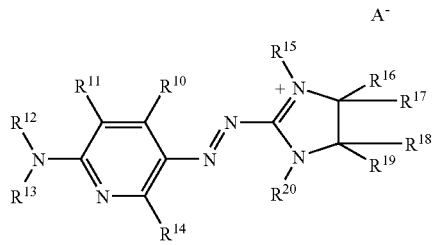

In the formula (2), $R^{10}$, $R^{11}$, $R^{14}$, $R^{16}$, $R^{17}$, $R^{18}$, and $R^{19}$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom. $R^{12}$, $R^{13}$, $R^{15}$ and $R^{20}$ each independently represents a hydrogen atom, alkyl group, or aryl group. $R^{10}$ and $R^{11}$; $R^{11}$ and $R^{12}$; $R^{12}$ and $R^{13}$; $R^{15}$ and $R^{16}$; $R^{16}$ and $R^{17}$; $R^{17}$ and $R^{18}$; $R^{18}$ and $R^{19}$; and $R^{19}$ and $R^{20}$ may join to each other to form a ring structure. $A^-$ represents a counter anion.

The alkyl group represented by $R^{10}$, $R^{11}$, $R^{12}$, $R^{13}$, $R^{14}$, $R^{15}$, $R^{16}$, $R^{17}$, $R^{18}$, $R^{19}$, and $R^{20}$ may be not-substituted or have a substituent. In a case where the alkyl group further has a substituent, the substituent is, for example, preferably an alkyl group, phenyl group, halogen atom, alkoxy group, aryloxy group, alkoxy carbonyl group, acyloxy group, acylamino group, carbamoyl group, cyano group, carboxylic acid group, sulfonic acid group, or heterocyclic group and, more preferably, a methyl group.

The alkyl group represented by $R^{10}$, $R^{11}$, $R^{12}$, $R^{13}$, $R^{14}$, $R^{15}$, $R^{16}$, $R^{17}$, $R^{18}$, $R^{19}$, and $R^{20}$ includes, preferably, for example, a methyl group, ethyl group, normal propyl group, isopropyl group, normal butyl group, isobutyl group, tertiary butyl group, pentyl group, cyclopentyl group, hexyl group, cyclohexyl group, heptyl group, octyl group, tertiary octyl group, 2-ethylhexyl group, decyl group, dodecyl group, octadecyl group.

As the alkyl group represented by $R^{10}$, $R^{11}$, $R^{12}$, $R^{13}$, $R^{14}$, $R^{15}$, $R^{16}$, $R^{17}$, $R^{18}$, $R^{19}$, and $R^{20}$, alkyl groups having 1 to 20 carbon atoms are preferred, alkyl groups having 1 to 15 carbon atoms are more preferred, alkyl groups having 1 to 10 carbon atoms are further preferred, and a methyl group, butyl group or heptyl group is particularly preferred.

The aryl group represented by $R^{10}$, $R^{11}$, $R^{12}$, $R^{13}$, $R^{14}$, $R^{15}$, $R^{16}$, $R^{17}$, $R^{18}$, $R^{19}$ and $R^{20}$ may be not-substituted or have a substituent and aryl groups having 6 to 25 carbon atoms are preferred, aryl groups having 6 to 10 carbon atoms are more preferred and, further, not-substituted or substituted phenyl groups are preferred.

In a case where the aryl group represented by $R^{10}$, $R^{11}$, $R^{12}$, $R^{13}$, $R^{14}$, $R^{15}$, $R^{16}$, $R^{17}$, $R^{18}$, $R^{19}$, and $R^{20}$ has a substituent, the substituent is, for example, preferably an alkyl group, phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

As the aryl group represented by $R^{10}$, $R^{11}$, $R^{12}$, $R^{13}$, $R^{14}$, $R^{15}$, $R^{16}$, $R^{17}$, $R^{18}$, $R^{19}$, and $R^{20}$, phenyl group, 2,4,6-trimethoxyphenyl group, or 2,6-isopropylphenyl group is particularly preferred.

The alkoxy group represented by $R^{10}$, $R^{11}$, $R^{14}$, $R^{16}$, $R^{17}$, $R^{18}$, and $R^{19}$ may be not-substituted or have a substituent. In a case where the alkoxy group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The alkoxy group represented by $R^{10}$, $R^{11}$, $R^{14}$, $R^{16}$, $R^{17}$, $R^{18}$, and $R^{19}$ preferably includes, for example, a methoxy group, ethoxy group, normal propyloxy group, isopropyloxy group, normal butyloxy group, isobutyloxy group, tertiary butyloxy group, pentyloxy group, cyclopentyloxy group, hexyloxy group, cyclohexyloxy group, hyeptyloxy group, octyloxy group, tertiary octyloxy group, 2-ethylhexyloxy group, decyloxy group, dodecyloxy group, octadecyloxy group, 1-ethylpropyloxy group, or 2-methyl-4,4-dimethylpentyloxy group.

As the alkoxy group represented by $R^{10}$, $R^{11}$, $R^{14}$, $R^{16}$, $R^{17}$, $R^{18}$, and $R^{19}$, alkoxy groups having 1 to 20 carbon atoms are preferred, alkoxy groups having 1 to 15 carbon atoms are more preferred, and a methoxy group is particularly preferred.

The aryloxy group represented by $R^{10}$, $R^{11}$, $R^{14}$, $R^{16}$, $R^{17}$, $R^{18}$, and $R^{19}$, may be not-substituted or have a substituent. As the aryloxy group, aryloxy groups having 6 to 25 carbon atoms are preferred, aryloxy groups having 6 to 10 carbon atoms are more preferred and, further, not-substituted or substituted phenoxy groups are preferred.

In a case where the aryloxy group represented by $R^{10}$, $R^{11}$, $R^{14}$, $R^{16}$, $R^{17}$, $R^{18}$, and $R^{19}$ further has a substituent, the substituent is, for example, preferably an alkyl group, phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

As the aryloxy group represented by $R^{10}$, $R^{11}$, $R^{14}$, $R^{16}$, $R^{17}$, $R^{18}$, and $R^{19}$, a phenoxy group is particularly preferred.

The alkylsulfonyl group represented by $R^{10}$, $R^{11}$, $R^{14}$, $R^{16}$, $R^{17}$, $R^{18}$, and $R^{19}$ may be not-substituted or have a substituent. In a case where the alkylsulfonyl group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The alkylsulfonyl group represented by $R^{10}$, $R^{11}$, $R^{14}$, $R^{16}$, $R^{17}$, $R^{18}$, and $R^{19}$ preferably includes, for example, a methylsulfonyl group, ethylsulfonyl groups, normal propylsulfonyl group, isopropylsulfonyl group, normal butylsulfonyl group, isobutylsulfonyl group, tertiary butylsulfonyl group, pentylsulfonyl group, cyclopentylsulfonyl group, hexylsulfonyl group, cyclohexylsulfonyl group, heptylsulfonyl group, octylsulfonyl group, tertiary octylsulfonyl group, 2-ethylhexyl sulfonyl group, decylsulfonyl group, dodecylsulfonyl group, or octadecylsulfonyl group.

As the alkylsulfonyl group represented by $R^{10}$, $R^{11}$, $R^{14}$, $R^{16}$, $R^{17}$, $R^{18}$, and $R^{19}$, alkylsulfonyl groups having 1 to 20 carbon atoms are preferred, alkylsulfonyl groups having 1 to 15 carbon atoms are more preferred, alkylsulfonyl groups having 1 to 10 carbon atoms are further preferred, and a methylsulfonyl group is particularly preferred.

The arylsulfonyl group represented by $R^{10}$, $R^{11}$, $R^{14}$, $R^{16}$, $R^{17}$, $R^{18}$, and $R^{19}$ may be not-substituted or have a substituent. Arylsulfonyl groups having 6 to 25 carbon atoms are preferred, arylsulfonyl groups having 6 to 10 carbon atoms are more preferred and, further, not-substituted or substituted phenyl sulfonyl groups are preferred.

In a case where the arylsulfonyl group represented by $R^{10}$, $R^{11}$, $R^{14}$, $R^{16}$, $R^{17}$, $R^{18}$, and $R^{19}$ further has a substituent, the substituent is, for example, preferably, an alkyl group, phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

As the arylsuofonyl group represented by $R^{10}$, $R^{11}$, $R^{14}$, $R^{16}$, $R^{17}$, $R^{18}$, and $R^{19}$, a phenylsulfonyl group is particularly preferred.

The alkylthio group represented by $R^{10}$, $R^{11}$, $R^{14}$, $R^{16}$, $R^{17}$, $R^{18}$, and $R^{19}$ may be not-substituted or have a substituent. In a case where the alkylthio group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The alkylthio group represented by $R^{10}$, $R^{11}$, $R^{14}$, $R^{16}$, $R^{17}$, $R^{18}$, and $R^{19}$, preferably includes, for example, a methylthio group, ethylthio group, normal propylthio group, isopropylthio group, normal butylthio group, isobutylthio group, tertiary butylthio group, pentylthio group, cyclopentylthio group, hexylthio group, cyclohexylthio group, heptylthio group, octylthio group, tertiary octylthio group, 2-ethylhexylthio group, decylthio group, dodecylthio group, or octadecylthio group.

As the alkylthio group represented by $R^{10}$, $R^{11}$, $R^{12}$, $R^{14}$, $R^{16}$, $R^{17}$, $R^{18}$, and $R^{19}$, alkylthio groups having 1 to 20 carbon atoms are preferred, alkylthio groups having 1 to 15 carbon atoms are more preferred, alkylthio groups having 1 to 10 carbon atoms are further preferred, a methylthio group is particularly preferred.

The arylthio group represented by $R^{10}$, $R^{11}$, $R^{14}$, $R^{16}$, $R^{17}$, $R^{18}$, and $R^{19}$ may be not-substituted or have a substituent. Arylthio groups having 6 to 25 carbon atoms are preferred, arylthio groups having 1 to 15 carbon atoms are more preferred and, further, not-substituted or substituted pherylthio groups are preferred.

In a case where the arylthio group represented by $R^{10}$, $R^{11}$, $R^{14}$, $R^{16}$, $R^{17}$, $R^{18}$, and $R^{19}$ further has a substituent, the substituent is, for example, preferably an alkyl group, phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

As the arylthio group represented by $R^{10}$, $R^{11}$, $R^{14}$, $R^{16}$, $R^{17}$, $R^{18}$, and $R^{19}$, a phenylthio group is particularly preferred.

The acyl group represented by $R^{10}$, $R^{11}$, $R^{14}$, $R^{16}$, $R^{17}$, $R^{18}$, and $R^{19}$ may be not-substituted or have a substituent. In a case where the acyl group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The acyl group represented by $R^{10}$, $R^{11}$, $R^{14}$, $R^{16}$, $R^{17}$, $R^{18}$, and $R^{19}$, preferably includes, for example, methyl carbonyl group, ethyl carbonyl group, normal propyl carbonyl group, isopropyl carbonyl group, normal butyl carbonyl group, isobutyl carbonyl group, tertiary butyl carbonyl group, pentyl carbonyl group, cyclopentyl carbonyl group, hexyl carbonyl group, cyclohexyl carbonyl group, heptyl carbonyl group, octyl carbonyl group, tertiary octylthio group, 2-ethylhexyl carbonyl group, decyl carbonyl group, dodecyl carbonyl group, octadecyl carbonyl group, 1-ethylpropyl carbonyl group, or 2-methyl-4,4-dimethylpentyl carbonyl group.

As the acyl group represented by $R^{10}$, $R^{11}$, $R^{14}$, $R^{16}$, $R^{17}$, $R^{18}$, and $R^{19}$, acyl groups having 1 to 20 carbon atoms are preferred, acyl groups having 1 to 15 carbon atoms are more preferred and a methylcarbonyl group is particularly preferred.

The carbamoyl group represented by $R^{10}$, $R^{11}$, $R^{14}$, $R^{16}$, $R^{17}$, $R^{18}$, and $R^{19}$ may be not-substituted or have a substituent. In a case where the carbamoyl group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The acyl group represented by $R^{10}$, $R^{11}$, $R^{14}$, $R^{16}$, $R^{17}$, $R^{18}$, and $R^{19}$, preferably includes, for example, methyl carbamoyl group, ethyl carbamoyl group, normal propyl carbamoyl group, isopropyl carbamoyl group, normal butyl carbamoyl group, isobutyl carbamoyl group, tertiary butyl carbamoyl group, pentyl carbamoyl group, cyclopentyl carbamoyl group, hexyl carbamoyl group, cyclohexyl carbamoyl group, heptyl carbamoyl group, octyl carbamoyl group, tertiary octyl carbamoyl group, 2-ethylhexyl carbamoyl group, dimethyl carbamoyl group, diethyl carbamoyl group, dinormal propyl carbamoyl group, diisopropyl carbamoyl group or dinormal butyl carbamoyl group.

As the carbamoyl group represented by $R^{10}$, $R^{11}$, $R^{14}$, $R^{16}$, $R^{17}$, $R^{18}$, and $R^{19}$, carbamoyl groups having 1 to 20 carbon atoms are preferred, carbamoyl groups having 1 to 15 carbon atoms are more preferred, and a carbonyl group is particularly preferred.

The amino group represented by $R^{10}$, $R^{11}$, $R^{14}$, $R^{16}$, $R^{17}$, $R^{18}$, and $R^{19}$ may be not-substituted or have a substituent. In a case where the amino group further has a substituent, the substituent is, for example, preferably, a phenyl group, halogen atom, alkoxy group, aryloxy group, alkoxycarbonyl group, acyloxy group, acylamino group, carbamoyl group, cyano group, carboxylic acid group, sulfonic acid group, or heterocyclic group.

The amino group represented by $R^{10}$, $R^{11}$, $R^{14}$, $R^{16}$, $R^{17}$, $R^{18}$, and $R^{19}$ may be primary or secondary and preferably includes, for example, methylamino group, ethylamino group, normal propylamino group, isopropylamino group, normal butylamino group, isobutylamino group, tertiary butylamino group, pentylamino group, cyclopentylamino group, hexylamino group, cyclohexylamino group, heptylamino group, octylamino group, tertiary octylamino group, 2-ethylhexylamino group, dimethylamino group, diethylamino group, dinormal propylamino group, diisopropylamino group, dinormal butylamino group, phenylamino group, or tolylamino group.

As the amino group represented by $R^{10}$, $R^{11}$, $R^{14}$, $R^{16}$, $R^{17}$, $R^{18}$, and $R^{19}$, amino groups having 1 to 20 carbon atoms are preferred, amino groups having 1 to 15 carbon atoms are more preferred, and a phenylamino group is particularly preferred.

The halogen atom represented by $R^{10}$, $R^{11}$, $R^{14}$, $R^{16}$, $R^{17}$, $R^{18}$, and $R^{19}$ includes preferably, for example, F, Cl, Br and I. Cl is particularly preferred.

In the formula (2), $R^{10}$ and $R^{11}$, $R^{11}$ and $R^{12}$, $R^{12}$ and $R^{13}$, $R^{15}$ and $R^{16}$, $R^{16}$ and $R^{17}$, $R^{17}$ and $R^{18}$, $R^{18}$ and $R^{19}$, and $R^{19}$ and $R^{20}$ may join to each other to form a ring structure. The ring structure includes, for example, pyrrolidine group, indoline group, cyclohexyl group, pyrazine group, and benzene.

In the formula (2), $A^-$ represents a counter anion. The counter anion represented by $A^-$ is not particularly restricted so long as it can form a counter anion, and it may be either a monoanion or polyvalent anion or may be either an inorganic anion or organic anion. Specifically, $Cl^-$, $Br^-$, or $I^-$, sulfate anion of 1 to 20 carbon atoms, carbonate anion of 2 to 21 carbon atoms, alkyl sulfate ion, hexafluoro phosphate ion, tetrafluoro borate ion, perchlorate ion, carbonate ion, or sulfate ion is preferred, and hexafluoro phosphate ion is more preferred.

In a case where $R^{15}$ or $R^{20}$ has a substituent, the substituent may form a salt instead of the counter anion represented by $A^-$ in which the azo compound is constituted as an intra-molecular salt. In a case where the substituent forms a salt instead of the counter anion represented by $A^-$, the azo compound of the invention may not have $A^-$.

A preferred embodiment of the azo compound of the second invention includes:
(5) an embodiment in which $R^{15}$ and $R^{20}$ represent aryl groups,
(6) an embodiment in which $R^{12}$ and $R^{13}$ represent an alkyl group or an aryl group,
(7) an embodiment in which $R^{11}$, $R^{14}$, $R^{16}$, $R^{17}$, $R^{18}$, and $R^{19}$ each independently represents a hydrogen atom, alkyl group, or aryl group, and
(8) an embodiment in which each of $R^{11}$, $R^{14}$, $R^{16}$, $R^{17}$, $R^{18}$, and $R^{19}$ represents hydrogen atom.

In the invention, each of the embodiments (5) to (8), or an embodiment having a combination of (5) to (6) and (7) or (8) is preferred.

Specifically, a preferred embodiment of the azo compound of the second invention is an embodiment in which $R^{10}$ represents an alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom and each of $R^{11}$, $R^{14}$, $R^{17}$, and $R^{18}$ represents hydrogen atom; or an embodiment in which $R^{10}$ represents a methyl group and each of $R^{11}$, $R^{14}$, $R^{17}$, and $R^{13}$ represents hydrogen atom in $R^{10}$, $R^{11}$, $R^{14}$, $R^{16}$, $R^{17}$, $R^{18}$, and $R^{19}$. Further, for $R^{12}$ and $R^{13}$, an embodiment in which they represent butyl group, cyclobutyl group, dibutyl carbamoyl, methyl group or butyloxycarbonylmethyl group or represent a pyrrolidine ring, or indoline ring in a case of cyclic structure is particularly preferred.

Azo compounds and tautomer thereof described above of the first and the second invention are also compounds (including azo pigments) having brilliant and favorable hues and excellent in light fastness and can be used suitably as azo dyes.

Specific examples of azo compounds of the first and the second invention represented by the formula (1) and the formula (2) (Exemplified compound D-1 to D48) are to be shown. However, they are not restrictive in the invention.

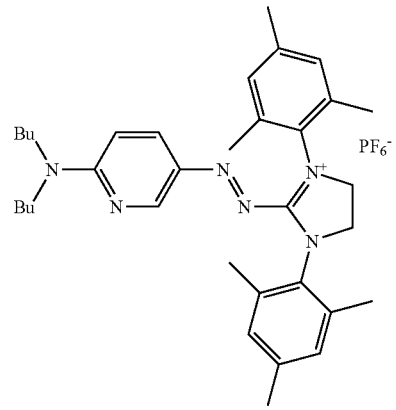

D-1

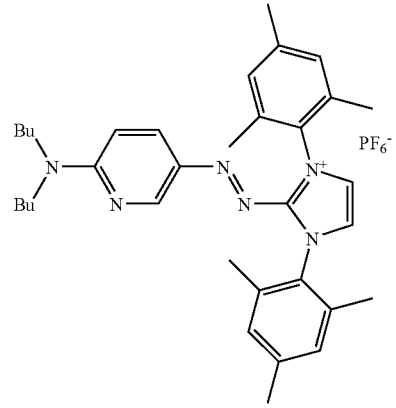

D-2

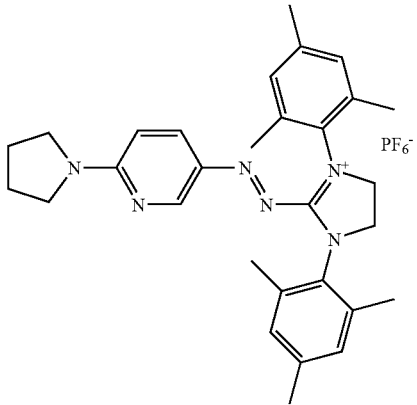

D-3

D-4
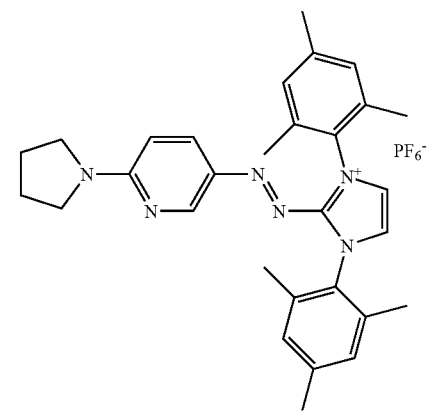
D-5
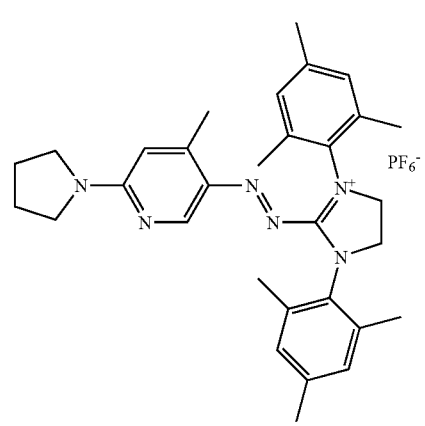
D-6
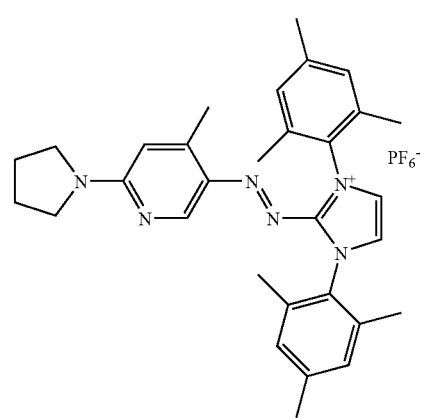
D-7
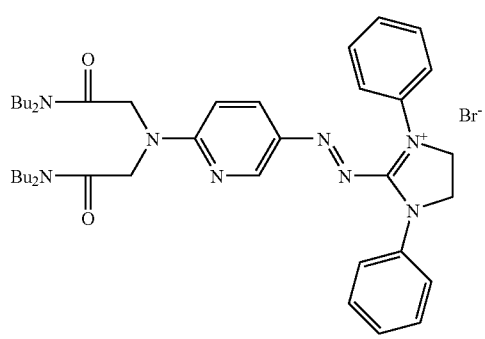
D-8
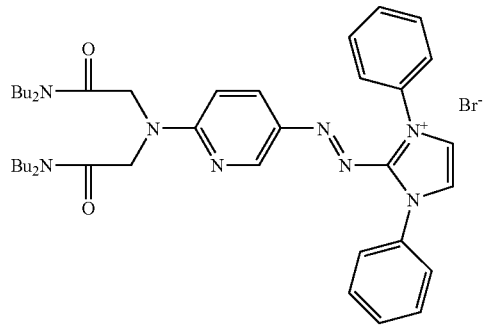
D-9
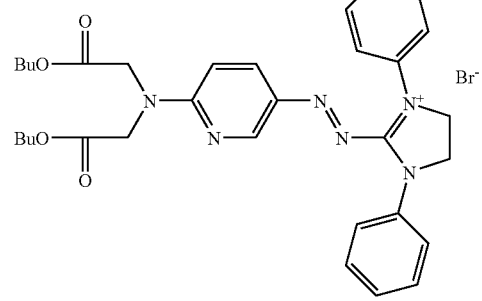
D-10
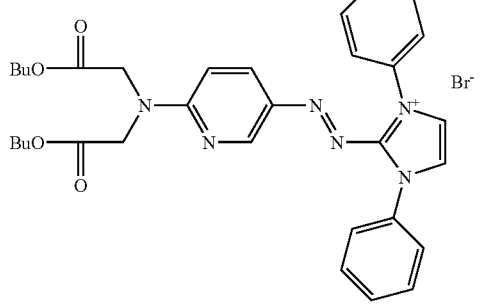
D-11
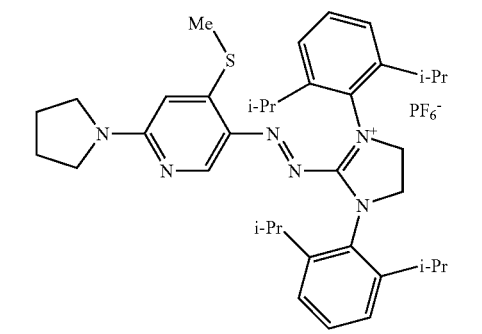
D-12
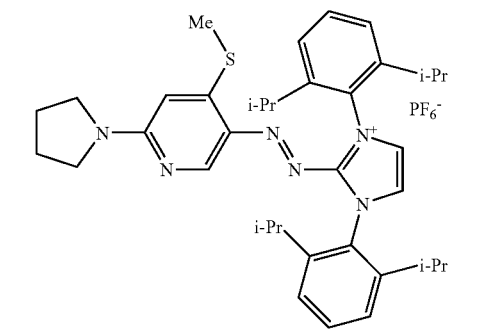

-continued

D-13, D-14, D-15, D-16, D-17, D-18, D-19, D-20, D-21

-continued
D-22
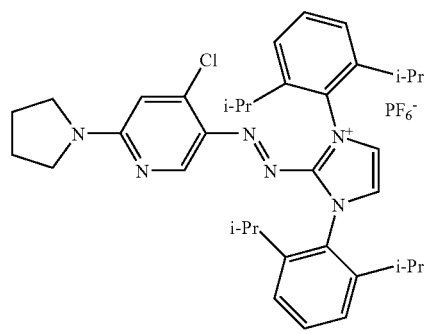
D-23
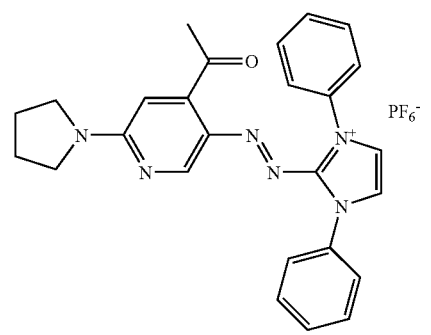
D-24
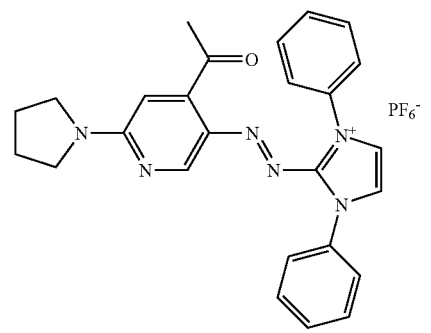
D-25
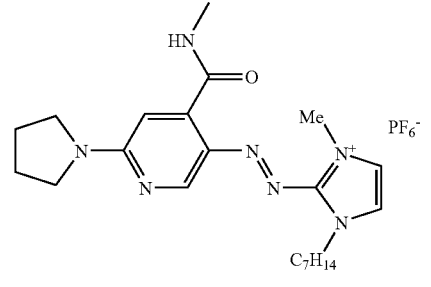
D-26
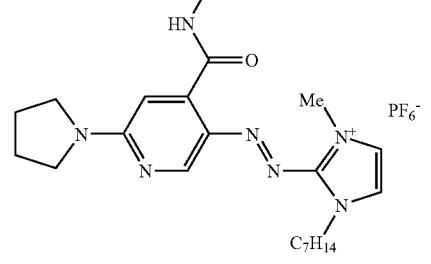
-continued
D-27
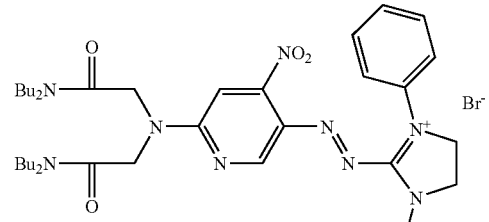
D-28
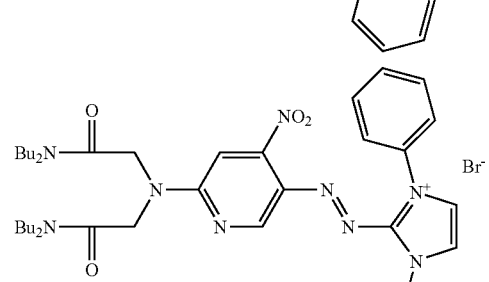
D-29
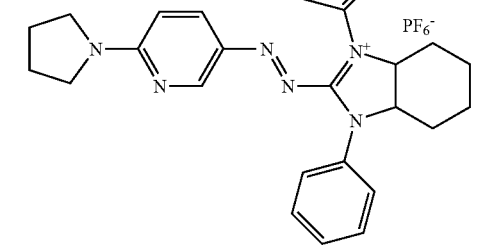
D-30
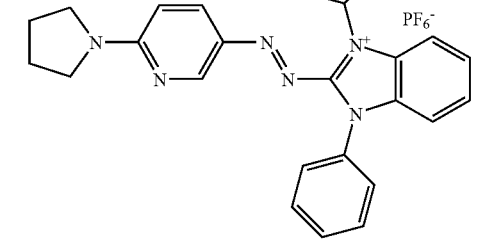
D-31
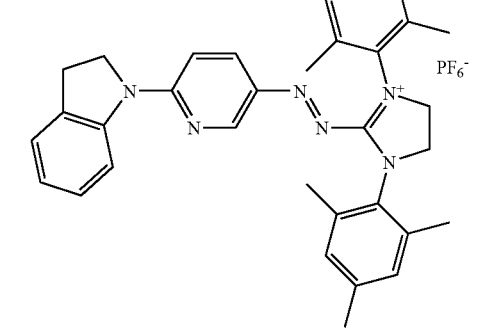

-continued
D-32
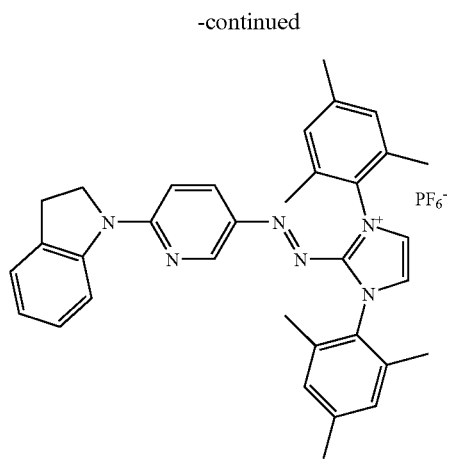
D-33
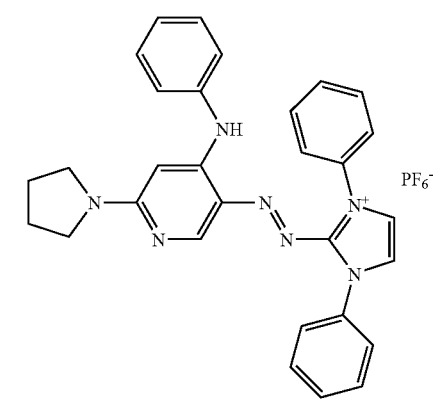
D-34
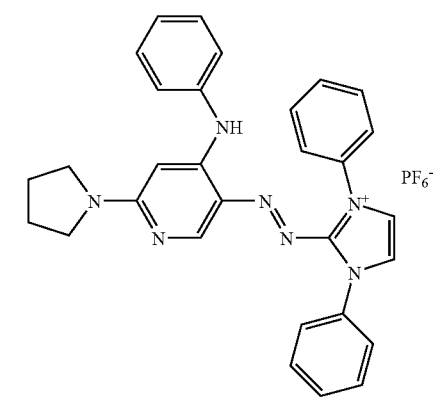
D-35
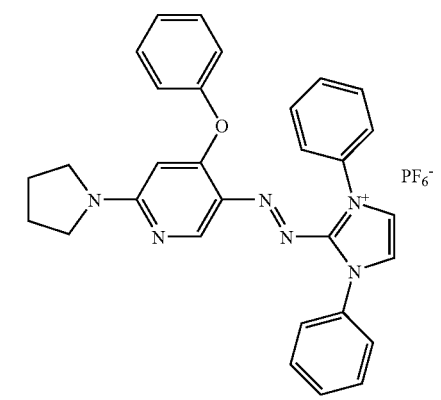
-continued
D-36
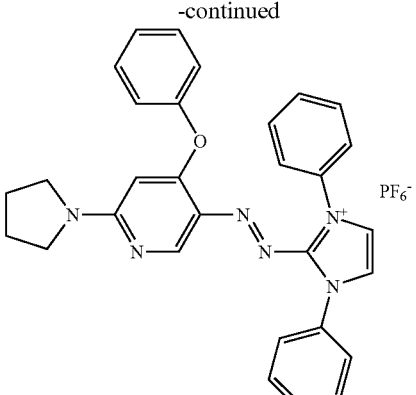
D-37
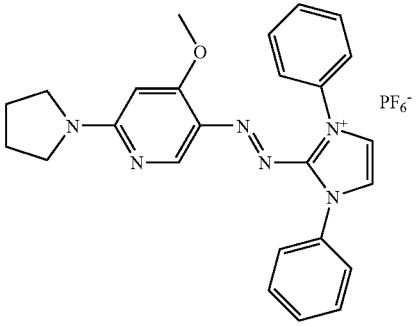
D-38
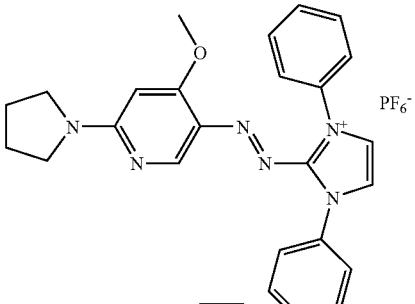
D-39
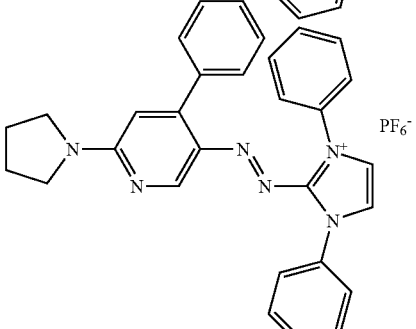
D-40
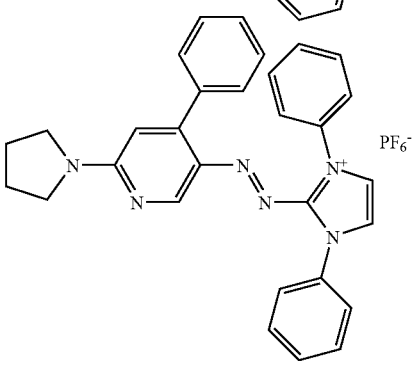

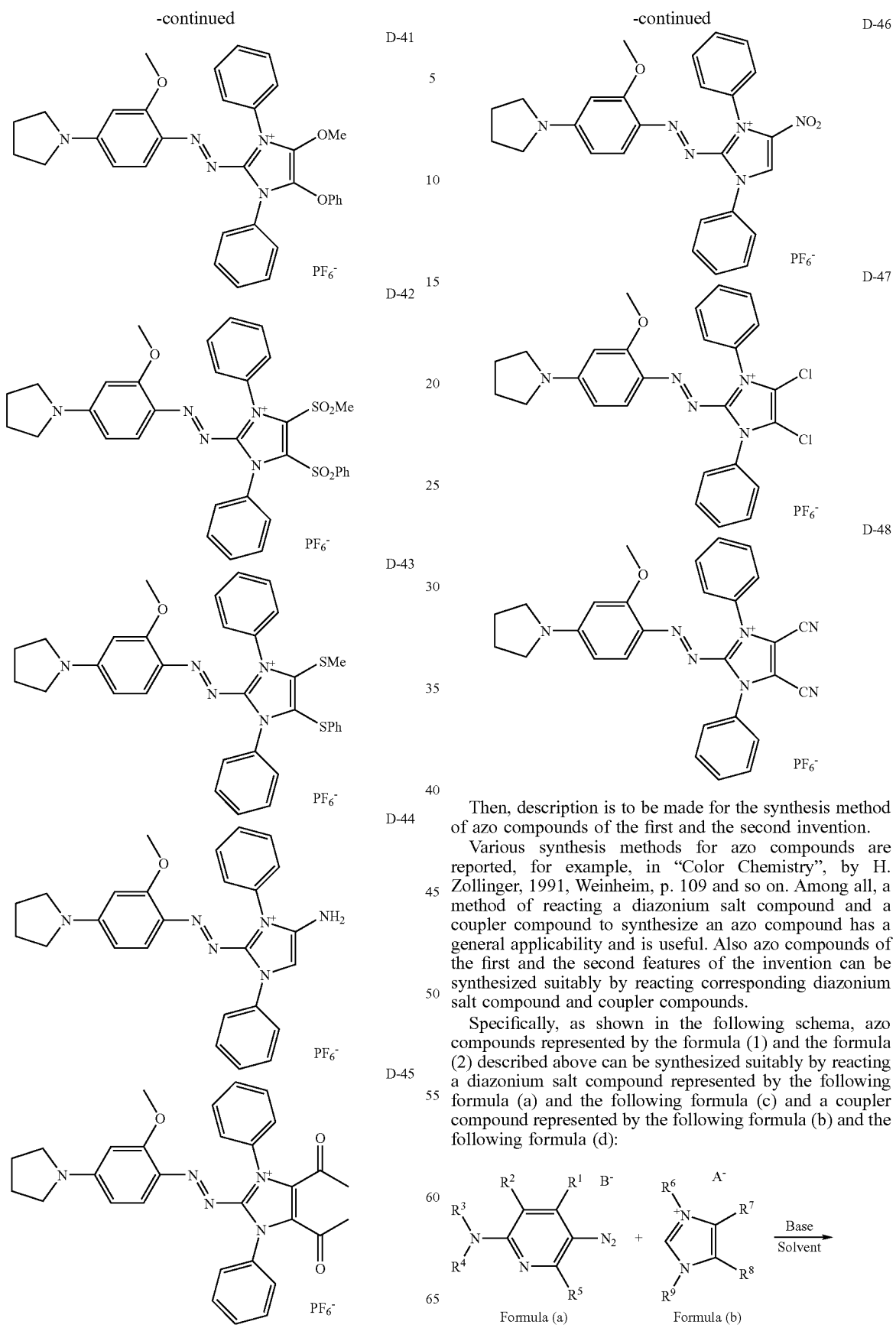

Then, description is to be made for the synthesis method of azo compounds of the first and the second invention.

Various synthesis methods for azo compounds are reported, for example, in "Color Chemistry", by H. Zollinger, 1991, Weinheim, p. 109 and so on. Among all, a method of reacting a diazonium salt compound and a coupler compound to synthesize an azo compound has a general applicability and is useful. Also azo compounds of the first and the second features of the invention can be synthesized suitably by reacting corresponding diazonium salt compound and coupler compounds.

Specifically, as shown in the following schema, azo compounds represented by the formula (1) and the formula (2) described above can be synthesized suitably by reacting a diazonium salt compound represented by the following formula (a) and the following formula (c) and a coupler compound represented by the following formula (b) and the following formula (d):

-continued

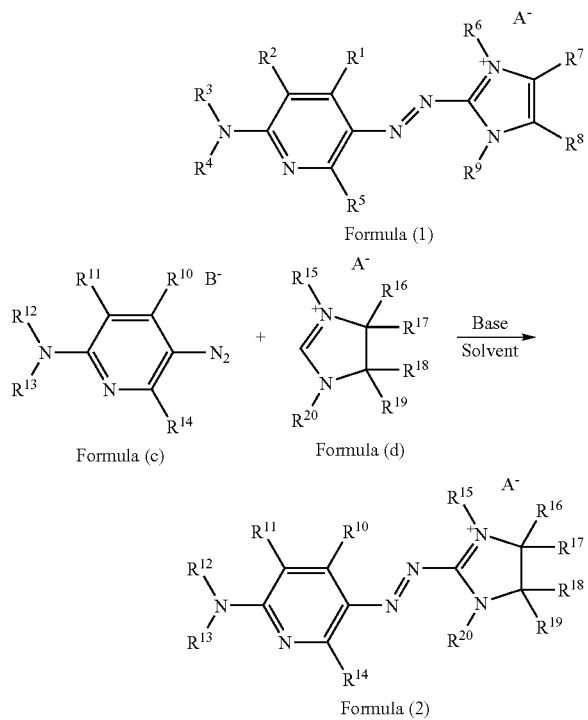

Formula (1)

Formula (c)   Formula (d)

Formula (2)

$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}$, and $A^-$ described in the schema have identical meanings as those for $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}$, and $R^{20}$, and $A^-$ in the formula (1) and the formula (2) described previously. $B^-$ in the formula (a) and the formula (b) represents a counter anion and represents, for example, $Cl^-$, $Br^-$, $PF_6^-$, or $BF_4^-$.

As the diazonium salt compound and the coupler compound used for the synthesis of azo compounds of the first and the second invention, an ionic solution marketed by Wako Pure Chemicals Ltd. (trade name of products: 1,3-bis(2,6-diisopropylphenyl)imidazolium chloride), etc. can be used for instance.

Various solvents can be used for the synthesis. The solvent includes, for example, water, alcohol, ethyl acetate, ether, and tetrahydrofuran (hereinafter referred to as "THF"). Further, with an aim of improving the yield, organic or inorganic base may be present together. The base includes, for example, sodium hydroxide, ammonia, triethylamine, pyridine, sodium hydrogen carbonate, and sodium methoxide.

As the conditions for reacting the diazonium salt compound represented by the formula (a) and the coupler compound represented by the formula (b), it is preferred that the coupler compound is added within a range from 1.0 to 1.1 equivalent amount based on one molar equivalent amount of the diazonium salt and they are preferably reacted at a reaction temperature of from 0° to room temperature. Further, since the diazonium salt is decomposed by light, it is preferred to use a vessel capable of shielding light as a reaction vessel, or conduct reaction in a dark room.

Azo compounds of the first and the second invention include azo dyes. The azo dyes include azo dyestuffs and azo pigments. The azo dyes are dyes having favorable absorption spectrum, showing good and brilliant hues and excellent also in the light fastness. Accordingly, azo compounds of the first and the second features of the invention can be used suitably, for example, as azo dyes showing good and brilliant hues and excellent in the light fastness.

Further, azo compounds of the first and the second features of the invention (including azo dyes) are suitable, for example, in application such as dyes for coloring synthetic resins, subliming thermal transfer materials or inks used for printing or ink jet recording or, further, functional dyes in the field of electronics.

EXAMPLE

The present invention is to be described more specifically by way of examples but the invention is not restricted to the following examples unless it exceeds the gist of the invention.

Example 1

As shown below, 2.36 g of the following coupler (b) was dissolved in 50 ml of THF, to which 1.9 g of a diazonium salt (a) was added. 0.7 g of diazabicyclo undecene (hereinafter referred to as "DBU") was further added to them, and then, they were stirred at 0° C. for one hour. 200 ml of water and 200 ml of ethyl acetate were added to the reaction solution and extracting operation was conducted. Then, after concentration of the organic layer, it was purified by column chromatography to synthesize Exemplified Compound D-1 as the azo compound of the invention described above.

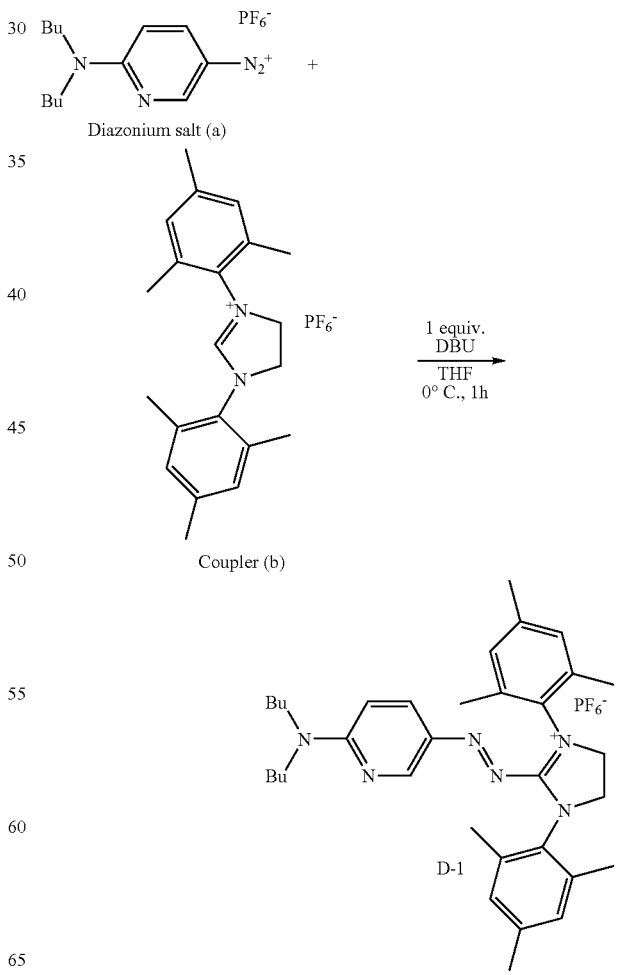

¹H-NMR data for the obtained azo compound (Exemplified Compound D-1) are shown below.

¹H-NMR (300 MHz, CDCl₃) δ0.92 (t, 6H), 1.23~1.42 (m, 4H), 1.51~1.64 (m, 4H), 2.23 (s, 12H), 2.28 (s, 6H), 3.42 (t, 2H), 3.71 (t, 2H), 4.21 (s, 4H), 6.55 (d, 1H), 6.93 (s, 4H), 7.42 (d, 1H), 7.98 (bs, 1H)

Example 2

Exemplified Compound D-2 as the azo compound of the invention was synthesized by the same method as in Example 1 except for using 2.3 g of the following coupler (c) instead of 2.3 g of the coupler (b) of Example 1.

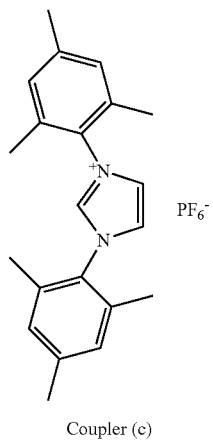

Coupler (c)

¹H-NMR data for the obtained azo compound (Exemplified Compound D-2) are shown below.

¹H-NMR (300 MHz, CDCl₃) δ0.94 (t, 6H), 1.21~1.43 (m, 4H), 1.53~1.65 (m, 4H), 2.06 (s, 12H), 2.41 (s, 6H), 3.42 (bs, 2H), 3.71 (bs, 2H), 6.52 (d, 1H), 7.03 (s, 4H), 7.44 (d, 1H), 7.52 (s, 2H), 7.98(bs, 1H)

Example 3

Exemplified Compound D-3 as the azo compound of the invention was synthesized by the same method as in Example 1 except for using 1.6 g of the following diazonium salt (d) instead of 1.9 g of the diazonium salt (a) of Example 1.

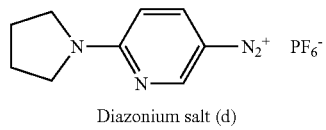

Diazonium salt (d)

¹H-NMR data for the obtained azo compound (Exemplified Compound D-3) are shown below.

¹H-NMR (300 MHz, CDCl₃) δ1.97~2.18 (m, 4H), 2.24 (s, 12H), 2.30 (s, 6H), 3.57 (t, 2H), 3.79 (t, 2H), 4.21 (s, 4H), 6.48 (d, 2H), 6.91 (s, 4H), 7.41 (d, 1H), 7.97 (bs, 1H)

Example 4

Exemplified Compound D-4 as the azo compound of the invention was synthesized by the same method as in Example 1 except for using 1.6 g of the diazonium salt (d) instead of 1.9 g of the diazonium salt (a) of Example 1 and using 2.3 g of the coupler (c) instead of 2.3 g of the coupler (b) of Example 1.

¹H-NMR data for the obtained azo compound (Exemplified Compound D-4) are shown below.

¹H-NMR (300 MHz, CDCl₃) δ1.98~2.17 (m, 16H), 2.40 (s, 6H), 3.52 (t, 2H), 3.73 (t, 2H), 6.44 (s, 1H), 7.01 (s, 4H), 7.43 (bs, 1H), 7.48 (s, 2H), 7.90 (s, 1H)

Example 5

Exemplified Compound D-5 as the azo compound of the invention was synthesized by the same method as in Example 1 except for using 1.7 g of the following diazonium salt (e) instead of 1.9 g of the diazonium salt (a) of Example 1.

Diazonium salt (e)

¹H-NMR data for the obtained azo compound (Exemplified Compound D-5) are shown below.

¹H-NMR (300 MHz, CDCl₃) δ1.63 (s, 3H), 1.93~2.02 (m, 2H), 2.04~2.18 (m, 2H), 2.24 (s, 12H), 2.29 (s, 6H), 3.54 (t, 2H), 3.73 (t, 2H), 4.39 (s, 4H), 6.24 (s, 1H), 6.92 (s, 4H), 8.28 (bs, 1H)

Example 6

Exemplified Compound D-6 as the azo compound of the invention was synthesized in the same manner as in Example 1 except for using 1.7 g of the diazonium salt (e) instead of 1.9 g of the diazonium salt (a) of Example 1 and using 2.3 g of the coupler (c) instead of 2.3 g of the coupler (b) of Example 1.

¹H-NMR data for the obtained azo compound (Exemplified Compound D-6) are shown below.

¹H-NMR (300 MHZ, CDCL₃) Δ1.64 (S, 3H), 1.97~2.17 (M, 16H), 2.39 (S, 6H), 3.50 (T, 2H), 3.72 (T, 2H), 6.21 (S, 1H), 7.01 (S, 4H), 7.44 (S, 2H), 8.30 (BS, 1H)

Example 7

Exemplified Compound D-31 as the azo compound of the invention was synthesized by the same method as in Example 1 except for using 1.8 g of the following diazonium salt (f) instead of 1.9 g of the diazonium salt (a) of Example 1.

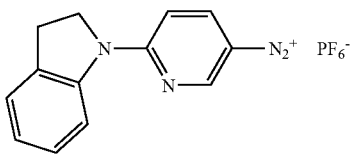

Diazonium salt (f)

¹H-NMR data for the obtained azo compound (Exemplified Compound D-31) are shown below.

$^1$H-NMR (300 MHz, CDCl$_3$) δ2.25 (s, 12H), 2.32 (s, 6H), 3.35 (t, 2H), 4.18 (t, 2H), 4.42 (s, 4H), 6.72 (bs, 1H), 6.91 (s, 4H), 7.14 (t, 1H), 7.21 (d, 2), 7.51 (dd, 1H), 8.11 (s, 1H), 8.50 (bs, 1H)

Example 8

Exemplified Compound D-32 as the azo compound of the invention was synthesized in the same manner as in Example 1 except for using 1.8 g of the diazonium salt (f) instead of 1.9 g of the diazonium salt (a) of Example 1 and using 2.3 g of the coupler (c) instead of 2.3 g of the coupler (b) of Example 1.

$^1$H-NMR data for the obtained azo compound (Exemplified Compound D-32) are shown below.

$^1$H-NMR (300 MHz, CDCl$_3$)δ2.08 (s, 12H), 2.21 (s, 6H), 3.31 (t, 2H), 4.19 (t, 2H), 6.79 (d, 1H), 7.03~7.11 (m, 5H), 7.21~7.29 (m, 2H), 7.57 (s, 2H), 8.17 (s, 1H), 8.43 (bs, 1H)

Comparative Example 1

Evaluation to be described later was conducted by using the following Comparative Compound 3.

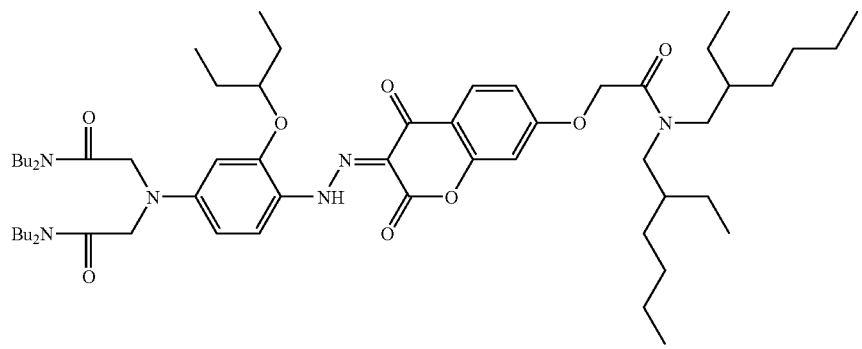

Comparative Compound 3

Comparative Example 2

Evaluation to be described later was conducted by using the following Comparative Compound 4.

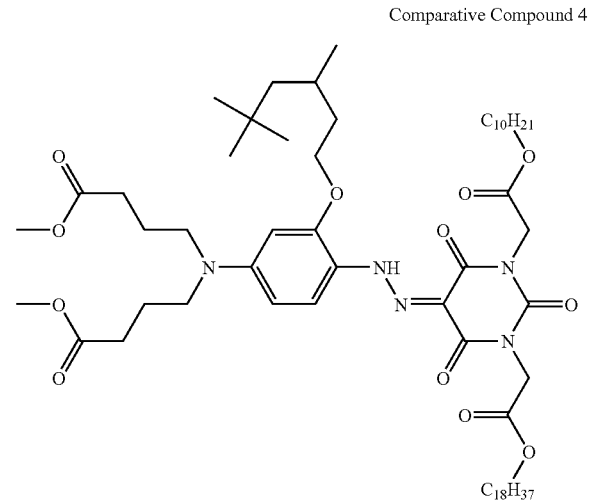

Comparative Compound 4

Evaluation (1) Absorptionon Spectrum

Chloroform/methanol (=1/1) solutions of azo compounds of Examples 1 to 8 and Comparative Examples 1 to 2 (2.0×10$^{-5}$ mol/L) were prepared respectively. They were taken each in a 1 cm square quartz cell and visible UV absorption spectrum was measured by using an absorption measuring apparatus (trade name of products: MPS-2400, manufactured by SHIMAZU CORP.). Thus, absorption maximum wavelength (λmax) was measured. Further, the absorption maximum was normalized and the width for Abs.=0.5 of the spectrum thereof was measured as the half-value width ($h_{1/2}$). It can be said that the hue is more brilliant and favorable as the value of the half-value width is smaller.

(2) Light Fastness Test of Solution

Butyl acetate solutions of azo compounds of Examples 1 to 8 and Comparative Examples 1 to 2 (2.0×10$^{-5}$ mol/L) were prepared respectively. They were taken each in a 1 cm square quartz cell and a xenon light was irradiated for 24 hours by using a merry go round type light fastness tester (manufactured by Eagle Engineering Co.) and the residual ratio after irradiation of the xenon light was determined based on the change of the visible UV absorption spectrum.

Results of the hue (λmax) of formed color and the light fastness are shown in the following Table 1.

TABLE 1

| | Azo compound | Hue of formed color λmax (nm) | Half-value width $h_{1/2}$ (nm) | Light fastness % |
|---|---|---|---|---|
| Example 1 | Compound D-1 | 481 | 82 | 94.5 |
| Example 2 | Compound D-2 | 528 | 98.5 | 92.6 |
| Example 3 | Compound D-3 | 476.5 | 80.5 | 94.4 |
| Example 4 | Compound D-4 | 504 | 99.5 | 88.6 |
| Example 5 | Compound D-5 | 494.5 | 115.5 | 92.1 |
| Example 6 | Compound D-6 | 519.5 | 120.5 | 80.5 |
| Example 7 | Compound D-31 | 548 | 125.5 | 90.8 |
| Example 8 | Compound D-32 | 568 | 117.5 | 89.2 |
| Comp. Example 1 | Comp. Compound 1 | 532 | 105 | 25 |
| Comp. Example 2 | Comp. Compound 2 | 527.5 | 106 | 31 |

As shown in the Table 1 above, azo compounds of the invention were excellent in the light fastness (durability against light) in comparison with the dye compounds used for comparison.

As described above according to the invention, novel azo compounds and tautomer thereof of favorable hue and excellent in light fastness can be provided.

The present invention has been achieved by obtaining a finding that the azo compound comprising the specified dye structure is excellent in the light fastness and by depending on such findings. The embodiments of the invention are as described below.

<1> An azo compound and tautomer thereof represented by the following formula (1):

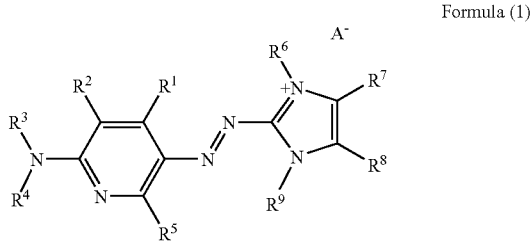

Formula (1)

wherein $R^1$, $R^2$, $R^5$, $R^7$, and $R^8$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom; $R^3$, $R^4$, $R^6$, and $R^9$ each independently represents a hydrogen atom, alkyl group, or aryl group; $R^1$ and $R^2$, $R^2$ and $R^3$, $R^3$ and $R^4$, $R^6$ and $R^7$, $R^7$ and $R^8$, and $R^8$ and $R^9$ may join to each other to form a ring structure; and $A^-$ represents a counter anion.

<2> The azo compound and tautomer thereof described in <1>, wherein each of $R^6$ and $R^9$ in the formula (1) is an aryl group.

<3> The azo compound and tautomer thereof described in <1>, wherein $R^3$ and $R^4$ in the formula (1) each independently represents an alkyl group or an aryl group.

<4> The azo compound and tautomer thereof described in <1>, wherein $R^2$, $R^5$, $R^7$, and $R^8$ in the formula (1) each independently represents a hydrogen atom, alkyl group, or aryl group.

<5> The azo compound and tautomer thereof described in <1>, wherein each of $R^2$, $R^5$, $R^7$, and $R^8$ in the formula (1) is a hydrogen atom.

<6> An azo compound and tautomer thereof represented by the following formula (2);

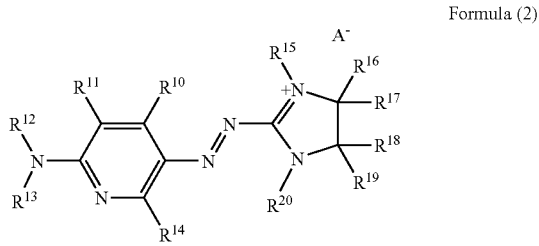

Formula (2)

wherein $R^{10}$, $R^{11}$, $R^{14}$, $R^{16}$, $R^{17}$, $R^{18}$, and $R^{19}$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group or halogen atom; $R^{12}$, $R^{13}$, $R^{15}$, and $R^{20}$ each independently represents a hydrogen atom, alkyl group, or aryl group; $R^{10}$ and $R^{11}$, $R^{11}$ and $R^{12}$, $R^{12}$ and $R^{13}$, $R^{15}$ and $R^{16}$, $R^{16}$ and $R^{17}$, $R^{17}$ and $R^{18}$, $R^{18}$ and $R^{19}$, and $R^{19}$ and $R^{20}$ may join to each other to form a ring structure; and $A^-$ represents a counter anion.

<7> The azo compound and tautomer thereof described in <6>, wherein each of $R^{15}$ and $R^{20}$ in the formula (2) is aryl group.

<8> The azo compound and tautomer thereof described in <6>, wherein $R^{12}$ and $R^{13}$ in the formula (2) each independently represents an alkyl group or an aryl group.

<9> The azo compound and tautomer thereof described in <6>, wherein $R^{11}$, $R^{14}$, $R^{16}$, $R^{17}$, $R^{18}$, and $R^{19}$ in the formula (2) each independently represents a hydrogen atom, alkyl group, or aryl group.

<10> The azo compound and tautomer thereof described in <6>, wherein each of $R^{11}$, $R^{14}$, $R^{16}$, $R^{17}$, $R^{18}$, and $R^{19}$ in the formula (2) is a hydrogen atom.

What is claimed is:

1. An azo compound or tautomer thereof represented by the following formula (1):

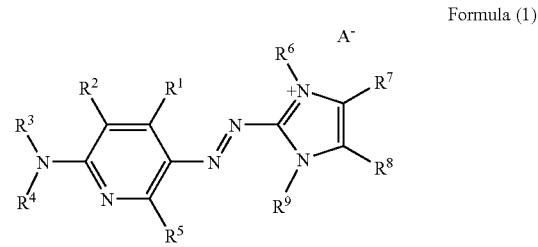

Formula (1)

wherein $R^1$, $R^2$, $R^5$, $R^7$, and $R^8$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom; $R^3$ and $R^4$ each independently represents a hydrogen atom, alkyl group, or aryl group; each of $R^6$ and $R^9$ is an aryl group; and $R^1$ and $R^2$, $R^2$ and $R^3$, $R^3$ and $R^4$, $R^6$ and $R^7$, $R^7$ and $R^8$, and $R^8$ and $R^9$ may join to each other to form a ring structure; and $A^-$ represents a counter anion.

2. The azo compound or tautomer thereof according to claim 1, wherein $R^3$ and $R^4$ in the formula (1) each independently represents an alkyl group or an aryl group.

3. An azo compound or tautomer thereof represented by the following formula (1):

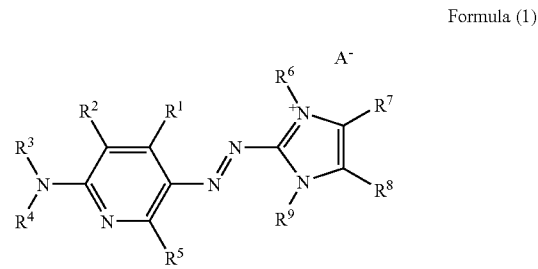

Formula (1)

wherein $R^1$ represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group, or halogen atom; $R^2$, $R^5$, $R^7$, and $R^8$ each independently represents a hydrogen atom, alkyl group, or aryl group; $R^3$, $R^4$, $R^6$, and $R^9$ each represents independently represents a hydrogen atom, alkyl group, or aryl group; and $R^1$ and $R^2$, $R^2$ and $R^3$, $R^3$ and $R^4$, $R^6$ and $R^7$, $R^7$ and $R^8$, and $R^8$ and $R^9$ may join to each other to form a ring structure; and $A^-$ represents a counter anion.

4. The azo compound or tautomer thereof according to claim 3, wherein each of $R^2$, $R^5$, $R^7$, and $R^8$ in the formula (1) is a hydrogen atom.

5. An azo compound or tautomer thereof represented by the following formula (2);

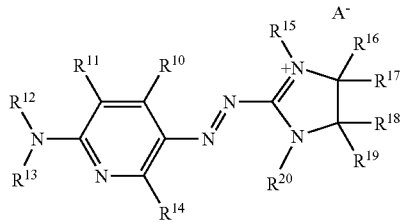

Formula (2)

wherein $R^{10}$, $R^{11}$, $R^{14}$, $R^{16}$, $R^{17}$, $R^{18}$, and $R^{19}$ each independently represents a hydrogen atom, alkyl group, aryl group, alkoxy group, aryloxy group, alkylsulfonyl group, arylsulfonyl group, alkylthio group, arylthio group, cyano group, acyl group, carbamoyl group, amino group, nitro group or halogen atom; $R^{12}$, $R^{13}$, $R^{15}$, and $R^{20}$ each independently represents a hydrogen atom, alkyl group, or aryl group; and $R^{10}$ and $R^{11}$, $R^{11}$ and $R^{12}$, $R^{12}$ and $R^{13}$, $R^{15}$ and $R^{16}$, $R^{16}$ and $R^{17}$, $R^{17}$ and $R^{18}$, $R^{18}$ and $R^{19}$, and $R^{19}$ and $R^{20}$ may join to each other to form a ring structure; and $A^-$ represents a counter anion.

6. The azo compound or tautomer thereof according to claim 5, wherein each of $R^{15}$ and $R^{20}$ in the formula (2) is aryl group.

7. The azo compound or tautomer thereof according to claim 5, wherein $R^{12}$ and $R^{13}$ in the formula (2) each independently represents an alkyl group or an aryl group.

8. The azo compound or tautomer thereof according to claim 5, wherein $R^{11}$, $R^{14}$, $R^{16}$, $R^{17}$, $R^{18}$, and $R^{19}$ in the formula (2) each independently represents a hydrogen atom, alkyl group, or aryl group.

9. The azo compound or tautomer thereof according to claim 5, wherein each of $R^{11}$, $R^{14}$, $R^{16}$, $R^{17}$, $R^{18}$, and $R^{19}$ in the formula (2) is a hydrogen atom.

* * * * *